(12) United States Patent
Nakatsui et al.

(10) Patent No.: US 12,060,321 B2
(45) Date of Patent: Aug. 13, 2024

(54) METHOD FOR PRODUCING INDIUM CARBOXYLATE

(71) Applicant: NIPPON CHEMICAL INDUSTRIAL CO., LTD., Tokyo (JP)

(72) Inventors: Kazuhiro Nakatsui, Tokyo (JP); Taiki Tsuzukiishi, Tamura-gun (JP)

(73) Assignee: NIPPON CHEMICAL INDUSTRIAL CO., LTD., Tokyo (JP)

( * ) Notice: Subject to any disclaimer, the term of this patent is extended or adjusted under 35 U.S.C. 154(b) by 546 days.

(21) Appl. No.: 17/602,065

(22) PCT Filed: Mar. 26, 2020

(86) PCT No.: PCT/JP2020/013618
§ 371 (c)(1),
(2) Date: Oct. 7, 2021

(87) PCT Pub. No.: WO2020/213359
PCT Pub. Date: Oct. 22, 2020

(65) Prior Publication Data
US 2022/0194889 A1  Jun. 23, 2022

(30) Foreign Application Priority Data
Apr. 16, 2019  (JP) .................................. 2019-077974

(51) Int. Cl.
*C07C 51/41* (2006.01)
(52) U.S. Cl.
CPC ............ *C07C 51/418* (2013.01); *C07C 51/41* (2013.01)
(58) Field of Classification Search
CPC ...... C07C 51/41; C07C 51/418; C07C 53/126
See application file for complete search history.

(56) References Cited

U.S. PATENT DOCUMENTS

| 2009/0264668 A1* | 10/2009 | Tokumitsu | ........... | C09K 11/565 |
| | | | | 423/299 |
| 2017/0137360 A1* | 5/2017 | Curley | ..................... | C07F 5/003 |
| 2020/0318002 A1* | 10/2020 | Peng | ....................... | H01L 33/06 |

FOREIGN PATENT DOCUMENTS

| JP | 2010-270139 A | 12/2010 |
| WO | 2017/201967 A1 | 11/2017 |

OTHER PUBLICATIONS

Franke et al., "The Unexpected Influence of Precursor Conversion Rate in the Synthesis of III-V Quantum Dots", Angewandte Chemie International Edition, 2015, vol. 54, No. 48, pp. 14299-14303, w/Supporting Information, cited in Specification and ISR (33 pages).

(Continued)

*Primary Examiner* — Yate' K Cutliff
(74) *Attorney, Agent, or Firm* — WHDA, LLP

(57) ABSTRACT

A method for producing an indium carboxylate of the present invention comprises the steps of reacting a hydroxyl group-containing indium carboxylate represented by Formula (1): $In(RCOO)_{3-x}(OH)_x$, wherein R is a straight chain or branched chain aliphatic group having 0 to 5 carbon atoms, and x is a number more than 0 and less than 3, with a lower carboxylic acid represented by the following Formula (2): R'COOH, wherein R' is a hydrogen atom or a straight chain or branched chain aliphatic group having 1 to 5 carbon atoms, and the hydrogen atom in the aliphatic group may be replaced with a halogen atom, so as to obtain a product; and then reacting the product with a higher carboxylic acid having 12 or more carbon atoms.

9 Claims, 2 Drawing Sheets

(56) References Cited

OTHER PUBLICATIONS

Wang et al., "Spectroscopic Properties of Colloidal Indium Phosphide Quantum Wires", J. Am. Chem. Soc., 2007, vol. 129, No. 46, pp. 14327-14335, w/Supporting Information, cited in Specification (45 pages).

Hu et al., The Synthesis and Characterization of Organoindium Complexes with Phenol or Chlorocarboxylate Ligands, Hecheng Huaxue, 2000, vol. 8, No. 1, pp. 79-82, w/English abstract, cited in ISR (4 pages).

International Search Report dated Jun. 9, 2020, issued in counterpart International Application No. PCT/JP2020/013618 (3 pages).

English machine translation of No. 3 of Non-Patent Literature Documents filed on Oct. 7, 2021; Hu et al., The Synthesis and Characterization of Organoindium Complexes with Phenol or Chlorocarboxylate Ligands, Hecheng Huaxue, 2000, vol. 8, No. 1, pp. 79-82, cited in ISR (4 pages).

\* cited by examiner

METHOD FOR PRODUCING INDIUM CARBOXYLATE

TECHNICAL FIELD

The present invention relates to a method for producing an indium carboxylate. The indium carboxylate produced by the present method is useful as, for example, a raw material for an InP quantum dot.

BACKGROUND ART

In recent years, development of quantum dots as light emitting material has progressed. As typical quantum dots, cadmium-based quantum dots such as CdSe, CdTe, and CdS are known, and these quantum dots have been developed from the viewpoint of excellent emission characteristics, etc. However, due to high toxicity and environmental load of cadmium, a cadmium-free quantum dot is expected to be developed.

Examples of the cadmium-free quantum dot include an InP (indium phosphide) quantum dot. As phosphorus components in production of an InP quantum dot, phosphine, an aminophosphine compound, a silylphosphine compound, etc., are often used as one of the raw materials. On the other hand, as indium components, an indium aliphatic carboxylate such as indium myristate and indium oleate is often used. The reasons for this include that an indium aliphatic carboxylate is hardly degraded by oxygen or water, and that an aliphatic carboxylic acid can play a role as colloidal stabilizer for InP quantum dots in a solvent.

Several methods for producing an indium aliphatic carboxylate have been proposed so far. For example, according to Patent Literature 1, an aliphatic indium carboxylate can be easily and industrially advantageously produced through a reaction between an indium alkoxide and an organic carboxylic acid anhydride. Further, as a general method, a method of producing an indium myristate through a reaction between indium acetate and myristic acid in a solvent is known (refer to Non Patent Literature 1 and Non Patent Literature 2).

CITATION LIST

Patent Literature

Patent Literature 1
  Japanese Patent Laid-Open No. 2010-270139

Non Patent Literature

Non Patent Literature 1
  Daniel Franke, Dr. Daniel K. et al., Angewandte Chemie, 2015, 54(48), 14299-14303
Non Patent Literature 2
  Fudong Wang, Heng Yu et al., J. Am. Chem. Soc., 2007, 129 (46), 14327-14335

SUMMARY OF INVENTION

Technical Problem

The method for producing an indium long-chain aliphatic carboxylate through a reaction between an indium short-chain carboxylate and a long-chain carboxylic acid as described in Non Patent Literature 1 and Non Patent Literature 2 is often used as a simple method. However, this method has a quality problem of the resulting indium aliphatic carboxylate. As a result, the InP quantum dots made from the indium aliphatic carboxylate by the method have a quality problem. Accordingly, an object of the present invention is to provide a method capable of producing an indium carboxylate having higher quality than the conventionally known method.

Solution to Problem

As a result of extensive study for solving the above problem, the present inventors have found that a short-chain indium carboxylate is unstable and a hydroxyl group-containing indium carboxylate is produced due to degradation. As a result of further research based on the finding, the present inventors have found that a high-quality indium carboxylate can be obtained by decreasing hydroxyl groups in the indium short-chain carboxylate generated due to degradation before subjecting to the reaction, so that the present invention has been completed.

The present invention has been made based on the finding described above to solve the problem, providing a method for producing an indium carboxylate including the steps of:

reacting a hydroxyl group-containing indium carboxylate represented by the following Formula (1):

$$In(RCOO)_{3-x}(OH)_x \qquad (1)$$

wherein R is a hydrogen atom or a straight chain or branched chain aliphatic group having 1 to 5 carbon atoms, and x is a number more than 0 and less than 3, with a lower carboxylic acid represented by the following Formula (2):

$$R'COOH \qquad (2)$$

wherein R' is a hydrogen atom or a straight chain or branched chain aliphatic group having 1 to 5 carbon atoms, and a hydrogen atom in the aliphatic group may be replaced with a halogen atom, so as to obtain a product; and then
reacting the product with a higher carboxylic acid having 12 or more carbon atoms.

Advantageous Effect of Invention

According to the present invention, a high-quality indium higher carboxylate can be obtained.

DESCRIPTION OF EMBODIMENT

Figure 1:
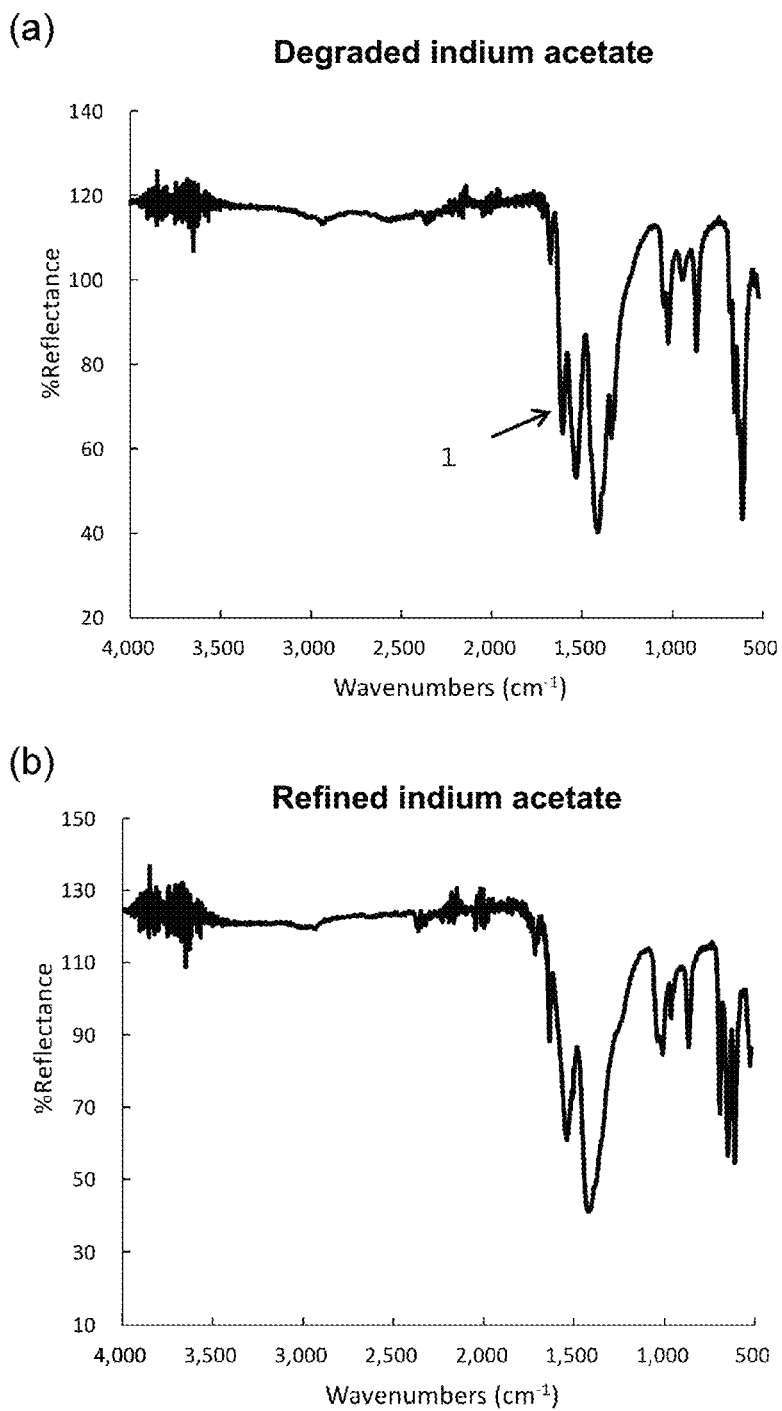
FIG. 1 (*a*) is an IR spectrum of hydroxyl group-containing indium acetate used as a raw material in Example 1, and FIG. 1 (*b*) is an IR spectrum of indium acetate that is a product of a first step in Example 1.

The present invention relates to a method for producing an indium salt of higher carboxylic acid. In the present invention, the higher carboxylic acid refers to a saturated or unsaturated aliphatic carboxylic acid having 12 or more carbon atoms. The salt of indium refers to a salt of In(III).

The present production method roughly includes the following two steps.

First Step:

A step of reacting an indium carboxylate containing a hydroxyl group represented by the following Formula (1):

$$In(RCOO)_{3-x}(OH)_x \qquad (1)$$

with a lower carboxylic acid represented by the following Formula (2):

$$R'COOH \qquad (2)$$

wherein R' is a hydrogen atom or a straight chain or branched chain aliphatic group having 1 to 5 carbon atoms, and at least one of the hydrogen atoms in the aliphatic group may be replaced with a halogen atom, so as to obtain a product.

Second Step

A step of reacting the product obtained in the first step with a higher carboxylic acid having 12 or more carbon atoms.

Each of the steps is described in detail below.

In the hydroxyl group-containing indium carboxylate represented by $In(RCOO)_{3-x}(OH)_x$ for use in the first step, R represents a hydrogen atom, or a straight chain or branched chain aliphatic group having 1 to 5 carbon atoms. As the straight chain or branched chain aliphatic group having 1 to 5 carbon atoms, a saturated or unsaturated aliphatic group may be used. For example, as R, a hydrogen atom or a straight chain or branched chain saturated aliphatic group having 1 to 5 carbon atoms may be used. Specifically, a group derived from formic acid, acetic acid, propionic acid, iso-butyric acid, butyric acid, iso-valeric acid, valeric acid or caproic acid may be used.

The hydroxyl group-containing indium carboxylate represented by Formula (1) is produced by degradation of indium carboxylate represented by $In(RCOO)_3$, wherein the definition of R is the same as described above. Degradation of $In(RCOO)_3$ occurs also when the compound is left in a normal air atmosphere at room temperature, and occurs even under environment suitable for storage such as a cool and dark room over time. The degree of deterioration may be evaluated by the degree of substitution of RCOO groups with OH groups in $In(RCOO)_3$. In other words, the degree of degradation of $In(RCOO)_3$ may be evaluated based on the value of x in Formula (1). The value of x takes any of more than 0 and less than 3, and the larger the value of x, the more the degradation of $In(RCOO)_3$ progresses. Also, as $In(RCOO)_3$ itself, a commercial high-purity product is easily available.

In the first step, a hydroxyl group-containing indium carboxylate represented by $In(RCOO)_{3-x}(OH)_x$ is reacted with a lower carboxylic acid represented by R'COOH. In the present invention, the "lower carboxylic acid" means a saturated or unsaturated carboxylic acid having 5 or less carbon atoms. The "lower carboxylic acid" is a monovalent carboxylic acid represented by R'COOH, and various derivatives such as salts and esters of R'COOH are not included in the lower carboxylic acid. R' is a hydrogen atom or a straight chain or branched chain aliphatic group having 1 to 5 carbon atoms. In the case where R' is a straight chain or branched chain aliphatic group having 1 to 5 carbon atoms, a saturated or unsaturated aliphatic group may be used as the aliphatic group. For example, as R', a hydrogen atom or a straight chain or branched chain saturated aliphatic group having 1 to 5 carbon atoms may be used. Specifically, a group derived from formic acid, acetic acid, propionic acid, iso-butyric acid, butyric acid, iso-valeric acid, valeric acid or caproic acid may be used.

In the case where R' is an aliphatic group, at least one of the hydrogen atoms in the aliphatic group may be replaced with a halogen atom. As the halogen atom, fluorine, chlorine, bromine or iodine may be used. In R', only one type of halogen atom may be present, or two or more types of halogen atoms may be present. Since a halogen atom has electron withdrawing properties, the acidity of a lower carboxylic acid represented by Formula (2) is enhanced by substitution of the hydrogen atom in R' with a halogen atom. As a result, the reaction between the lower carboxylic acid represented by Formula (2) and the hydroxyl group-containing indium carboxylate represented by Formula (1) is facilitated. From the viewpoint of further enhancing the advantage, it is preferable that at least one of the hydrogen atoms in the aliphatic group in R' be replaced with fluorine, and it is more preferable that all the hydrogen atoms in the aliphatic group be replaced with fluorine.

Alternatively, a small amount of such a lower carboxylic acid having enhanced acidity may be catalytically added for facilitating the reaction. In the case where a lower carboxylic acid substituted with a halogen atom is catalytically added, the amount added is preferably 0.01 mol or more and 10 mol or less, more preferably 0.05 mol or more and 5 mol or less, and still more preferably 0.1 mol or more and 1 mol or less, relative to 1 mol of the hydroxyl group in a hydroxyl group-containing indium carboxylate.

In the first step, it is preferable to use a lower carboxylic acid having the same RCOO group as that of a hydroxyl group-containing indium carboxylate represented by $In(RCOO)_{3-x}(OH)_x$. For example, being a lower carboxylic acid having the same RCOO as that of $In(RCOO)_{3-x}(OH)_x$ means that $CH_3COOH$ is used as the lower carboxylic acid in the case where a hydroxyl group-containing indium carboxylate is represented by $In(CH_3COO)_{3-x}(OH)_x$. The reaction between the hydroxyl group-containing indium carboxylate represented by Formula (1) and the lower carboxylic acid having the same RCOO has advantages that quality can be easily checked in the first step, and progress of a substitution reaction between the lower carboxylic acid and a higher carboxylic acid in the second step described below can be easily confirmed.

In the first step, it is also preferable to use a lower carboxylic acid having the same RCOO group as that of the hydroxyl group-containing indium carboxylate represented by $In(RCOO)_{3-x}(OH)_x$ (however, at least one of the hydrogen atoms in R is replaced with a halogen atom). As the halogen atom, fluorine, chlorine, bromine or iodine may be used. In R, only one type of halogen atom may be present, or two or more types of halogen atoms may be present. The advantage of the substitution of the hydrogen atom in R with a halogen atom is as described above. From the viewpoint of facilitating the reaction between the lower carboxylic acid represented by Formula (2) and the hydroxyl group-containing indium carboxylate represented by Formula (1), it is preferable that at least one of the hydrogen atoms in R be replaced with fluorine, and it is preferable that all the hydrogen atoms in R be replaced with fluorine.

It is preferable that the reaction between a hydroxyl group-containing indium carboxylate and a lower carboxylic acid be performed under conditions that the lower carboxylic acid is present in an amount equal to or more than the amount of the hydroxyl group-containing indium carboxylate. Through the reaction under such conditions, the substitution reaction between the hydroxyl group in the hydroxyl group-containing indium carboxylate and the R'COO group in the lower carboxylic acid easily proceeds, so that $In(RCOO)_{3-x}(R'COO)_x$ as indium carboxylate is successfully produced. From the viewpoint of further enhancing the advantage, the amount of the lower carboxylic acid relative to 1 mol of the hydroxyl group in the hydroxyl group-containing indium carboxylate is preferably 13 mol or more and 3000 mol or less, more preferably 1 mol or more and 1000 mol or less, and still more preferably 1 mol or more and 500 mol or less. The amount of the lower carboxylic acid is the sum of the amount of the lower carboxylic acid actually added and, in the case of using an acid anhydride described later, the amount of the lower carboxylic acid produced by the reaction between the acid anhydride and water.

When a hydroxyl group-containing indium carboxylate is reacted with a lower carboxylic acid, the lower carboxylic acid may be added to the hydroxyl group-containing indium carboxylate all at once or sequentially, or in an opposite manner, the hydroxyl group-containing indium carboxylic acid may be added to the lower carboxylic acid all at once or sequentially. Alternatively, both may be added all at once at the same time or sequentially. Whatever form of addition is employed, the reaction may be performed at room temperature, i.e., unheated conditions, or under heated conditions. In the case where the reaction is performed under heated conditions, the reaction temperature depends on the lower carboxylic acid for use, being controlled to preferably 30° C. or more and 200° C. or less, more preferably 50° C. or more and 150° C. or less, and still more preferably 80° C. or more and 120° C. or less, from the viewpoint of enhancing the reaction efficiency. The reaction time on this occasion is preferably 5 minutes or more and 600 minutes or less, more preferably 15 minutes or more and 300 minutes or less, and 30 minutes or more and 180 minutes or less from the viewpoint of obtaining a sufficient yield. In the case where the reaction is performed under heated conditions, it is preferable that the reaction be performed under refluxing conditions from the viewpoint of obtaining a high yield.

From the viewpoint of successful proceeding of the reaction between the hydroxyl group-containing indium carboxylate and the lower carboxylic acid, the reaction may be performed in an aprotic organic solvent or in a protic organic solvent having low nucleophilicity. Examples of the protic organic solvent include nitromethane. Examples of the aprotic organic solvent include acetone, acetonitrile, dimethylformamide, N-methylpyrrolidone, toluene, xylene, acetonitrile, dibutyl ether, cyclopentyl methyl ether, and chlorobenzene.

The reaction between a hydroxyl group-containing indium carboxylate and a lower carboxylic acid in the first step proceeds according to the following formula:

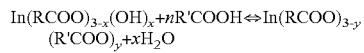

wherein x is the same as described above, y is a number more than 0 and 3 or less, and n is a number equal to x or more.

As shown in the reaction formula, a hydroxyl group-containing indium carboxylate reacts with a lower carboxylic acid to produce water as by-produced. The presence of water can affect the purity of $In(RCOO)_{3-y}(R'COO)_y$, which is the target product in the first step. It is therefore advantageous to remove water as by-product from the reaction system. From this viewpoint, it is preferable to allow coexistence of a dehydrating agent in the reaction between a hydroxyl group-containing indium carboxylate and a lower carboxylic acid. It is preferable that, an acid anhydride (an anhydride of monovalent carboxylic acid) be particularly used as the dehydrating agent, from the viewpoint of enhancing the purity of $In(RCOO)_{3-y}(R'COO)_y$ as target product in the first step, because a lower carboxylic acid is produced from the acid anhydride through a reaction with water produced as by-product, and the produced lower carboxylic acid is capable of reacting with the hydroxyl group-containing indium carboxylate. The acid anhydride used as dehydrating agent has a structure represented by $(R''CO)_2O$. R'' represents a hydrogen atom or a straight chain or branched chain aliphatic group having 1 to 5 carbon atoms. R'' may be the same as or different from R and/or R'. In other words, the anhydride of a carboxylic acid of the same as or different from the lower carboxylic acid may be used as dehydrating agent. From the viewpoint of further enhancing the purity of $In(RCOO)_{3-y}(R'COO)_y$ as target product in the first step, it is advantageous that R'' is the same as R', and it is advantageous that R'' is the same as R and R'. In other words, in the case where a hydroxyl group-containing indium carboxylate is represented by $In(RCOO)_{3-x}(OH)_x$, it is preferable that the lower carboxylic acid have the same RCOO group as that of the hydroxyl group-containing indium carboxylate, and the acid anhydride have the same RCO group as that of the hydroxyl group-containing indium carboxylate.

The amount of acid anhydride for use as dehydrating agent may be an amount capable of removing water produced as by-product of the reaction between a hydroxyl group-containing indium carboxylate and a lower carboxylic acid. Specifically, relative to 1 mol of the hydroxyl group of hydroxyl group-containing indium carboxylate, an acid anhydride in an amount of preferably 1 mol or more and 100 mol or less, more preferably 1 mol or more and 50 mol or less, and still more preferably 1 mol or more and 20 mol, is added to the reaction system.

Through the first step, a product containing $In(RCOO)_{3-y}(R'COO)_y$ is obtained. A second step is then performed to react the product with a higher carboxylic acid. When the product of the first step is reacted with the higher carboxylic acid, the higher carboxylic acid may be added into the product of the first step all at once or sequentially, or in an opposite manner, the product of the first step may be added into the higher carboxylic acid all at once or sequentially. Alternatively, both may be added all at once at the same time or sequentially.

In the second step, it is advantageous to use the higher carboxylic acid as solvent in addition to as a reactant. From this viewpoint, it is preferable to perform the reaction under conditions in which an excess amount of a higher carboxylic acid is present relative to $In(RCOO)_{3-y}(R'COO)_y$ contained in the product in the first step. Through the reaction under such conditions, an exchange reaction of the RCOO group and the R'COO group in $In(RCOO)_{3-y}(R'COO)_y$ with a higher carboxylic acid can proceed smoothly. From the viewpoint of further enhancing the advantage, the amount of the higher carboxylic acid is preferably 3 mol or more and 100 mol or less, more preferably 3 mol or more and 50 mol or less, and still more preferably 4 mol or more and 30 mol or less, relative to 1 mol of $In(RCOO)_{3-y}(R'COO)_y$.

The reaction may be performed at room temperature, i.e., unheated conditions, or under heated conditions. In the case where the reaction is performed under heated conditions, the reaction temperature is appropriately set depending on the higher carboxylic acid subjected to the reaction, and generally set to preferably 20° C. or more and 300° C. or less, more preferably 50° C. or more and 250° C. or less, and still more preferably 80° C. or more and 200° C. or less from the viewpoint of successful proceeding of the reaction. The reaction time on this occasion is preferably 10 minutes or more and 900 minutes or less, more preferably 30 minutes or more and 600 minutes or less, and 60 minutes or more and 300 minutes or less from the viewpoint of obtaining a sufficient yield.

Further, from the viewpoint of successful proceeding of the reaction in the second step, the reaction may be performed in an aprotic organic solvent or in a protic organic solvent having low nucleophilicity. Examples of the protic organic solvent include nitromethane. Examples of the aprotic organic solvent include acetone, acetonitrile, dimethylformamide, N-methylpyrrolidone, toluene, xylene, acetonitrile, dibutyl ether, cyclopentyl methyl ether, and chlorobenzene.

The higher carboxylic acid for use in the second step has 12 or more carbon atoms. As the higher carboxylic acid, a monovalent carboxylic acid or a polyvalent carboxylic acid may be used. In the case where indium carboxylate as target product of the present production method is used as a raw material for a quantum dot, it is advantageous to use a monovalent carboxylic acid as the higher carboxylic acid.

A monovalent higher carboxylic acid is represented by $R_1COOH$. In the formula, $R_1$ represents a straight chain or branched chain aliphatic group having 11 or more carbon atoms, preferably 11 or more and 19 or less carbon atoms. As the aliphatic group, a saturated or unsaturated aliphatic group may be used. In other words, as the higher carboxylic acid, a straight chain saturated or unsaturated carboxylic acid having 12 or more carbon atoms, preferably 12 or more and 20 or less carbon atoms, may be used.

In the case of using indium carboxylate that is the target product of the present production method as a raw material for a quantum dot, it is preferable that a straight chain or branched chain saturated aliphatic group having 11 or more carbon atoms, particularly 11 or more and 19 or less carbon atoms, be used as $R_1$. Specifically, it is preferable to use lauric acid, tridecylic acid, myristic acid, pentadecylic acid, palmitic acid, margaric acid, stearic acid, nonadecylic acid, arachidic acid or oleic acid. One of these higher carboxylic acids may be used alone, or two or more thereof may be used in combination.

The reaction in the second step proceeds according to the following formula.

$$In(RCOO)_{3-y}(R'COO)_y + 3R_1COOH \rightarrow In(R_1COO)_3 + (3-y)RCOOH + yR'COOH$$

As shown in the formula, the reaction produces RCOOH and R'COOH, i.e., lower carboxylic acids. Accordingly, through removal of the lower carboxylic acid from the reaction system, the reaction is further facilitated, so that the yield of $In(R_1COO)_3$ is enhanced. Since the lower carboxylic acid is known to be a compound having a low boiling point, a reaction system under reduced pressure is advantageous for removal of the lower carboxylic acid from the reaction system. Such a reaction system enables the lower carboxylic acid to be easily vaporized, so that removal from the reaction system can be easily achieved. From this viewpoint, the pressure of the reaction system in the second step is controlled to preferably 0.1 Pa or more and 10 kPa or less, particularly 0.5 Pa or more and 5 kPa or less, and particularly preferably 1 Pa or more and 1 kPa or less.

After completion of the reaction in the second step, acetone or the like as poor solvent is added to the reaction system to precipitate $In(R_1COO)_3$ as target product, which is an indium salt of a higher carboxylic acid. The precipitate is separated by filtration, subjected to repulp cleaning with an organic solvent, and dried to obtain high-purity indium carboxylate. It is preferable that the indium carboxylate be indium laurate, indium tridecylate, indium myristate, indium pentadecylate, indium palmitate, indium margarate, indium stearate, indium nonadecylate, indium arachidate or indium oleate, depending on the type of the higher carboxylic acid used in the second step.

The indium carboxylate thus obtained has no hydroxyl group in the structure, being suitable for use as a raw material for a quantum dot containing indium, for example for an InP quantum dot, in particular.

EXAMPLES

Hereinafter, the present invention is described in more detail with reference to Examples. However, the scope of the present invention is not limited to Examples. Unless otherwise specified, "%" means "mass %".

Example 1

First Step

Degraded indium acetate was used as a model hydroxyl group-containing indium carboxylate. Specifically, after opening a sealed container of commercially available indium acetate for use as reagent, the indium acetate was placed in a cool and dark place with a lid closed for about 100 days before use. The results of analysis using an ICP emission spectrometer (manufactured by Shimadzu Corporation) showed that the degraded indium acetate was composed of hydroxyl group-containing indium acetate represented by 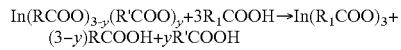. In a flask, 5 g of the degraded indium acetate, 160 g of acetic acid, and 9 g of acetic anhydride were placed and heated at 120° C. for 1.5 hours while refluxing. After completion of the reaction, the reaction product was separated by-filtration under a nitrogen atmosphere at room temperature, subjected to repuip cleaning with dehydrated hexane (manufactured by Kanto Chemical Co., Inc.), and further subjected to vacuum drying. The IR spectra of the degraded indium acetate used as a raw material and indium acetate as reaction product are shown in FIG. 1(a) and FIG. 1(b). It is shown that in FIG. 1(a), an absorption derived from the hydroxyl group of hydroxyl group-containing indium acetate (absorption indicated by an arrow 1 in the Figure 1(a), in the vicinity of 1600 cm$^{-1}$) is observed, whereas in FIG. 1(b), no absorption is observed. Accordingly, it is confirmed that through the first step, the hydroxyl group was removed from the hydroxyl group-containing indium acetate in the degraded indium acetate used as a raw material.

Second Step

Figure 2:
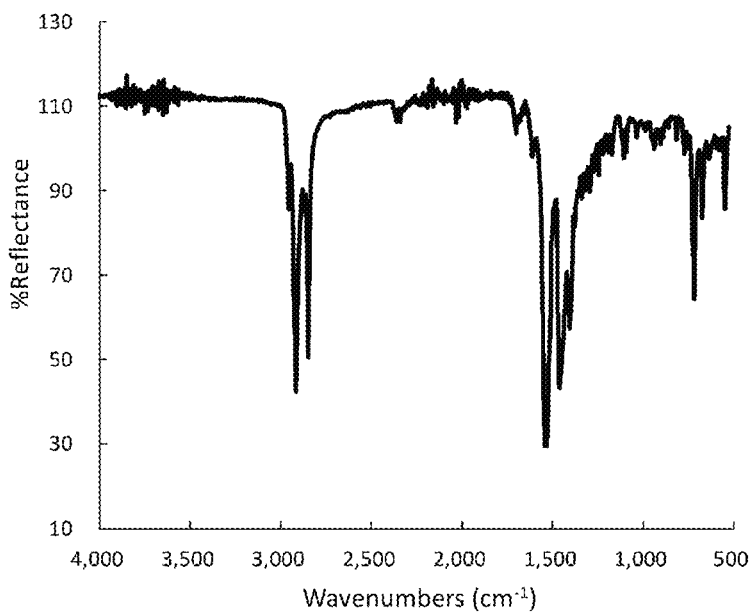
FIG. 2 is an IR spectrum of indium myristate that is a product of a second step in Example 1.

In a flask, 5.1 g of indium acetate obtained in the first step and 30 g of myristic acid were placed, and heated under reduced pressure at 110° C. for 3 hours and then at 150° C. for 1 hour. The pressure of the reaction system was set to 30 Pa or less. After completion of the reaction, acetone was added to the reaction system to precipitate indium myristate as reaction product. Subsequently, the reaction product was separated by filtration under a nitrogen atmosphere, subjected to repulp cleaning twice with dehydrated acetone (manufactured by Kanto Chemical Co., Inc.), subjected to rinse cleaning twice with dehydrated acetone (manufactured by Kanto Chemical Co., Inc.), subjected to rinse cleaning with dehydrated hexane (manufactured by Kanto Chemical Co., Inc.) and further dried under reduced pressure. In this way, 12.6 g of the target indium myristate was obtained. The IR spectrum of the indium myristate is shown in FIG. 2. As is clear from the results shown in the figure, no absorption derived from the hydroxyl group (in the vicinity of 1600 cm⁻¹) was observed in indium myristate, so that it was confirmed that no hydroxyl group was contained.

Comparative Example 1

Figure 3:
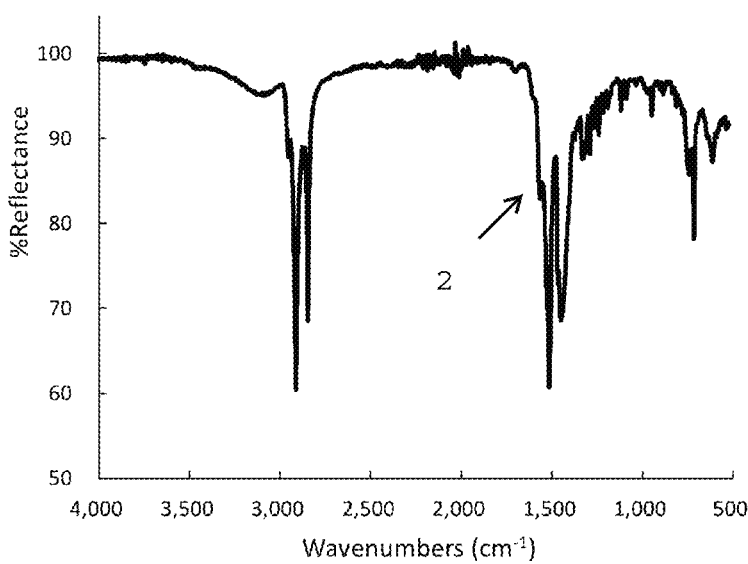
FIG. 3 is an IR spectrum of hydroxyl group-containing indium myristate that is a product in Comparative Example 1.

As a model hydroxyl group-containing indium carboxylate, one the same as the degraded indium acetate for use in Example 1 was used. The degraded indium acetate was not supplied to the first step in Example 1, but was supplied to the second step in the same Example. The IR spectrum of indium myristate thus obtained is shown in FIG. 3. As is clear from the results shown in the figure, an absorption derived from a hydroxyl group (absorption indicated by arrow 2 in the FIG. 3, in the vicinity of 1600 cm⁻¹) was observed in indium myristate, so that it was confirmed that the hydroxyl group was contained.

Example 2

As a model hydroxyl group-containing indium carboxylate, a one the same as the degraded indium acetate for use in Example 1 was used. In a flask, 44 g of the degraded indium acetate, 1.9 g of triflucroacetic acid, and 139.8 g of acetic anhydride were placed and heated at 50° C. for 2 hours. The same operation as in Example 1 was then performed to obtain a target indium myristate. In measurement of the IR spectrum of the indium myristate, no absorption derived from a hydroxyl group (in the vicinity of 1600 cm⁻¹) was observed, so that it was confirmed that no hydroxyl group was contained.

The invention claimed is:

1. A method for producing an indium carboxylate comprising the steps of:

reacting a hydroxyl group-containing indium carboxylate represented by the following Formula (1):

$$In(RCOO)_{3-x}(OH)_x \quad (1)$$

wherein R is a hydrogen atom or a straight chain or branched chain aliphatic group having 1 to 5 carbon atoms, and x is a number more than 0 and less than 3, with a lower carboxylic acid represented by the following Formula (2):

$$R'COOH \quad (2)$$

wherein R' is a hydrogen atom or a straight chain or branched chain aliphatic group having 1 to 5 carbon atoms, and at least one of the hydrogen atoms in the aliphatic group may be replaced with a halogen atom, so as to obtain a product; and then reacting the product with a higher carboxylic acid having 12 or more carbon atoms.

2. The method according to claim 1, wherein R is a hydrogen atom or a straight chain or branched chain saturated aliphatic group having 1 to 5 carbon atoms.

3. The method according to claim 1, wherein the hydroxyl group-containing indium carboxylate is reacted with the lower carboxylic acid under heated conditions.

4. The method according to claim 3, wherein the hydroxyl group-containing indium carboxylate and the lower carboxylic acid are reacted in the presence of an anhydride of carboxylic acid that is the same as or different from the lower carboxylic acid.

5. The method according to claim 1, wherein the product and the higher carboxylic acid are reacted under conditions at 0.1 Pa or more and 10 kPa or less, and at 20° C. or more and 300° C. or less.

6. The method according to claim 1, wherein the higher carboxylic acid is a straight chain saturated or unsaturated carboxylic acid having 12 or more and 20 or less carbon atoms.

7. The method according to claim 1, for producing indium laurate, indium tridecylate, indium myristate, indium pentadecylate, indium palmitate, indium margarate, indium stearate, indium nonadecylate, indium arachidate or indium oleate.

8. The method according to claim 1, wherein the lower carboxylic acid has an RCOO group the same as that in the hydroxyl group-containing indium carboxylate.

9. The method according to claim 1, wherein the lower carboxylic acid has an RCOO group the same as that in the hydroxyl group-containing indium carboxylate, wherein at least one of the hydrogen atoms in R is replaced with a halogen atom.

* * * * *